US008799020B2

(12) United States Patent
Roberts et al.

(10) Patent No.: US 8,799,020 B2
(45) Date of Patent: Aug. 5, 2014

(54) POS PRINTING TRIGGERED BY PHARMACY PRESCRIPTION ORDERS

(75) Inventors: Michael Roberts, Palm Harbor, FL (US); Michael Ebert, Naperville, IL (US)

(73) Assignee: Catalina Marketing Corporation, St. Petersburg, FL (US)

( * ) Notice: Subject to any disclaimer, the term of this patent is extended or adjusted under 35 U.S.C. 154(b) by 1109 days.

(21) Appl. No.: 11/761,813

(22) Filed: Jun. 12, 2007

(65) Prior Publication Data
US 2008/0306769 A1 Dec. 11, 2008

Related U.S. Application Data

(60) Provisional application No. 60/942,247, filed on Jun. 6, 2007.

(51) Int. Cl.
G06Q 10/00 (2012.01)
G06F 7/60 (2006.01)
G06G 7/58 (2006.01)
G06F 9/45 (2006.01)
A61B 5/00 (2006.01)
G06F 19/00 (2011.01)

(52) U.S. Cl.
USPC .................................. 705/3; 705/2

(58) Field of Classification Search
USPC ....................................... 705/2, 3, 4
See application file for complete search history.

(56) References Cited

U.S. PATENT DOCUMENTS

| 6,240,394 | B1* | 5/2001 | Uecker et al. ..................... 705/3 |
| 6,330,491 | B1* | 12/2001 | Lion .............................. 700/237 |
| 6,564,121 | B1 | 5/2003 | Wallace et al. |
| 6,759,366 | B2 | 7/2004 | Beckerdite et al. |
| 6,784,906 | B2 | 8/2004 | Long et al. |
| 6,836,843 | B2 | 12/2004 | Seroussi et al. |
| 2001/0047281 | A1 | 11/2001 | Keresman et al. |
| 2002/0111833 | A1* | 8/2002 | Dick .................................. 705/3 |
| 2003/0233256 | A1* | 12/2003 | Cardenas et al. .................. 705/3 |
| 2004/0081669 | A1* | 4/2004 | Greeven et al. ................ 424/400 |
| 2004/0215981 | A1 | 10/2004 | Ricciardi et al. |
| 2004/0225528 | A1* | 11/2004 | Brock .............................. 705/2 |
| 2005/0154641 | A1* | 7/2005 | Mortimer ........................ 705/14 |
| 2005/0261938 | A1* | 11/2005 | Silverbrook et al. ............. 705/2 |
| 2006/0229910 | A1 | 10/2006 | Longman et al. |

FOREIGN PATENT DOCUMENTS

WO    WO 2006/036712    4/2006

OTHER PUBLICATIONS

International Search Report PCT/US06/19432.
Written Opinion of International Searching Authority PCT/US06/19432.
International Search Report PCT/US06/14482.

(Continued)

Primary Examiner — Sean K Hunter
(74) Attorney, Agent, or Firm — Pillsbury Winthrop Shaw Pittman LLP

(57) ABSTRACT

A system and method for printing, at a POS of a retail store, information relating to a pharmacy prescription ordered in a pharmacy of said retail store, comprises determining in a PM CS of the pharmacy a payloadID to associate with a prescription order and printing by the PM CS information associated with said first prescription order. Then, a POS CS reading the printing at a POS of the retail store resulting in said POS CS printing a payload associated with the payloadID in the memory of the POS CS.

42 Claims, 8 Drawing Sheets

(56) References Cited

OTHER PUBLICATIONS

Written Opinion of International Searching Authority PCT/US06/14482.
Written Opinion of International Searching Authority PCT/IB2008/051766.
International Search Report PCT/IB2008/051766.
Feb. 28, 2005, English translation of unexamined patent publication No. KR 10-2005-0018739.
Jun. 1, 2002, English translation of examined patent publication No. KR 10-2002-0041225.

* cited by examiner

PM CS DATA STRUCTURES

Pharmacy Patient Records Table 500

| Pat ID | PresID | Patient Information | NDC | Qnty | Order date | Filled Date | Purchase or Disposal Date |
|---|---|---|---|---|---|---|---|
| | | | | | | | |

Pharmacy Patient Records Table 500 (continued)

| Purchase or Disposal date | Copay amount | Department number | RecordID | DrugID | DoctorID | NewRX |
|---|---|---|---|---|---|---|
| | | | | | | |

Pharmacy Patient Records Table 500 (continued)

| RefillRX | Refill# RX | PaymentType | Date processed | Time processed | NDC | Medication Name |
|---|---|---|---|---|---|---|
| | | | | | | |

Pharmacy Patient Records Table 500 (continued)

| Customer Name | Age | Date of Birth | Gender | Script Status | Payor | Payor Code |
|---|---|---|---|---|---|---|
| | | | | | | |

Pharmacy Patient Records Table 500 (continued)

| RX Number | Dispensed Qty | Refill Sequence | Language Indicator | Daily Supply | Days Supply | Original Fill Date |
|---|---|---|---|---|---|---|
| | | | | | | |

Pharmacy Patient Records Table 500 (continued)

| Expires Date | Refills Remaining | Unique Patient ID | Dr. Number | Monograph | State Code | Region |
|---|---|---|---|---|---|---|
| | | | | | | |

Pharmacy Patient Records Table 500 (continued)

| Retailer Division | Retailer Store | Patient Directions | Pharmacist Directions | NCPDP ID Number | BIN No. | Control No. |
|---|---|---|---|---|---|---|
| | | | | | | |

Pharmacy Patient Records Table 500 (continued)

| Agency | Group | Plan | Name Mask | Medicaid | Opt Out (HIPAA) | Duplicate |
|---|---|---|---|---|---|---|
| | | | | | | |

FIG. 5A

De Identified Pharmacy Patient Records Table 510

| EncPat ID | EncPresID | BF | NDC | Qnty | Order date | Filled Date | Purchase or Disposal Date |
|---|---|---|---|---|---|---|---|

De Identified Pharmacy Patient Records Table 510 (continued)

| Purchase or Disposal date | Copay amount | . . . |
|---|---|---|

Pharmacy Payload ID Table 520

| EncPresID | NDC | Qnty | Payload ID | Date1 | Date2 | RecordID |
|---|---|---|---|---|---|---|

Pharmacy Prescription Label Printer Table 530

| PresID | Prescription Label Information (Patient name, medicine name, dosing information) | Bar Code encoding Pres Payload ID and/or recordID |
|---|---|---|

Pharmacy Additional Information Printer Table 540

| NDC | Additional Information relating to NDC medication |
|---|---|

Pharmacy Stock Table 550

| NDC | Unit Type | Unit Quantity in stock |
|---|---|---|

Encrypted Patient ID table 560

| PatID | EncPatID |
|---|---|

Encrypted Prescription ID table 570

| PresID | EncPresID |
|---|---|

FIG. 5B

RS POS CS DATA STRUCTURES

RS Prescriptions Payload Table 600

| Payload ID | Payload | Date1 | Date2 |
|---|---|---|---|

RS Transaction Data Table 610

| TID | CID | Date | ProdID1 | ProdID1 Price | ProdID1 Qnty |
|---|---|---|---|---|---|

RS Transaction Data Table 610 (continued)

| ProdID2 | ProdID2 Price | ProdID2 Qnty | Transaction Total Price | Transaction Price Discounts |
|---|---|---|---|---|

RS POS Stock and Price Table 620

| ProdID (UPC) | Product Description | Stock Quantity | Price1 | Price2 |
|---|---|---|---|---|

FIG. 6

CENTRAL CS 10 DATA STRUCTURES

CENTRAL CS DATA STRUCTURES CORRESPONDING TO PM CS DATA STRUCTURES
    De Identified Pharmacy Patient Records Table 510A
    Pharmacy Payload ID Table 520A
    Pharmacy Additional Information Printer Table 540A CENTRAL CS DATA STRUCTURES CORRESPONDING TO RS POS CS DATA STRUCTURES
    RS Payload Table 600A
    RS Transaction Data Table 610A

ADDITIONAL CENTRAL CS TABLES

Payload Criteria Table 710

| RSID | NDC | Payload | | | | |
|---|---|---|---|---|---|---|
| | | | | | | |

Payload Criteria Table 720

| RSID | NDC1 | DATE1 | NDC2 | DATE2 | NDC3 | DATE3... | Payload |
|---|---|---|---|---|---|---|---|
| | | | | | | | |

Combined Payload Table 730

| RSID | EncPresID | EncPatID | NDC | PayloadID | Payload | Date1 | Date2 |
|---|---|---|---|---|---|---|---|
| | | | | | | | |

FIG. 7

POS PRINTING TRIGGERED BY PHARMACY PRESCRIPTION ORDERS

CROSS REFERENCE TO RELATED APPLIATIONS

This application claims priority to provisional application 60/942,247, filed Jun. 6, 2007.

BACKGROUND OF THE INVENTION

1. Field of the Invention
The field of the invention is POS computer systems.
2. Background
U.S. Pat. No. 6,304,849 discloses a method and system for printing a combination pharmaceutical label and directed newsletter. U.S. Pat. No. 6,240,394 discloses a method and apparatus for automatically generating advisory information for pharmacy patients. U.S. Pat. No. 6,067,524 discloses a method and system for automatically generating advisory information for pharmacy patients along with normally transmitted data. U.S. Pat. No. 6,321,210 discloses a method and apparatus for selective distribution of discount coupons.

This invention relates to pharmacy management computer systems and retail store point of sale computer systems.

ACRONYMS AND ABBREVIATIONS USED HEREIN

CS—Computer System
PM CS Pharmacy Management Computer System
Retail Store—RS
NDC—National Drug Code
UPC—Universal Product Code
POS—Point of Sale
POS CS—Point of Sale Computer System
ID—Identification
CID—Consumer ID
RSID—Retail Store ID
PatID—Patient ID
ProdID—Product ID
PresID—Prescription ID
DrugID—Identification of a drug
PayloadID—Payload Identification
EncPresID—Encrypted Prescription ID
EncPatID—Encrypted Patient ID
Qnty—Quantity
BF—Bland Field
TID—Transaction ID

DEFINITIONS USE HEREIN

A CS means one or more computers having commonly accessible data storage.

A computer means at least an input device for inputting data, a central processing unit for processing data, a memory for storing data, and an output device for outputting data.

A POS CS is a CS designed to log purchase transactions occurring in a store at least one POS, and to track inventory for the store.

A PM CS is a computer system designed to log and track prescription orders in a pharmacy and track pharmacy medication inventory.

UPCs mean any set of codes each one uniquely identifying a product.

OBJECTS OF THE INVENTION

It is an object of this invention to enable a retail store to process purchase transactions including purchase of prescriptions.

It is an object of this invention to enable a retail store to print payloads based upon pharmacy prescription data for a prescription order being purchased.

SUMMARY OF THE INVENTION

This application provides methods and systems to enable a POS CS of a retail store having a pharmacy to process purchase transactions including purchase of prescriptions filled by the pharmacy, at a POS, and to enable a printer at the POS to print payloads during that purchase transaction that are based upon pharmacy prescription data for a prescription order being purchased in the transaction. A payload is printed information intended for the person purchasing the prescription.

In a first embodiment, the PM CS responds to receipt of a prescription order by storing information including a payloadID on a recording media, such as in a printed bar code printed on paper or magnetization pattern imposed in magnetic media, for the prescription order. A person or machine attaches the recording media to the filled prescription for that prescription order. The recording media and filled prescription are then presented at a POS of the POS CS, for purchase of the filled prescription. During a transaction to purchase the filled prescription, the POS CS reads the payloadID at the POS. The POS CS previously stored an association of payloadIDs to payloads. The POS CS identifies the payload associated therein with the payloadID read from the recording media and prints that payload during the purchase transaction involving the prescription.

In a second embodiment, the PM CS stores in the PM CS memory a unique record identifier (RecordID) in association with each record of data for each prescription order. The PM CS also stores the RecordID on recording media, such as a printed bar code printed on paper or a magnetization pattern imposed in magnetic media. A person or a machine attaches the recording media to the filled prescription. The recording media and filled prescription are then presented at a POS of the POS CS, for purchase of the filled prescription. During the transaction to purchase the filled prescription, the POS CS reads the RecordID at the POS. Then, the POS CS transmits the RecordID to the PM CS. In response, the PM CS retrieves from memory certain information from the PM CS prescription order record associated with that recordID and transmits that retrieved certain information to the POS CS. That certain information includes a payloadID. The POS CS identifies the payload associated with the received payloadID and prints that payload during the purchase transaction involving the prescription.

In the first and second embodiments, the POS CS preferably receives from the PM CS during the transaction for purchase of the filled prescription: Prescription ID; Copay amount; NDC; and Department number. In the first embodiment, that information is encoded in the recording media attached to the filled prescription. Attaching is by means of hardware such as bags, staples, clips, or by adhesives, such as sticky tape or glues. In the second embodiment, that information may all be retrieved to the POS CS from the PM CS during the transaction in response to the PM CS receiving the RecordID.

In a first alternative, a payloadID corresponds to information associated in the PM CS with the prescription order.

For example, in the first alternative, the payloadID may correspond to a drug identification (drugID), such as an NDC for the drug specified in the prescription order. In this example, a payloadID is a drugID or an encrypted version of the DrugID, and the drugID may be an NDC. The PM CS associates with each prescription order, the payloadID corresponding to the drug identified in the prescription order. The corresponding payload provides printed information about the drug specified by the prescription, and optionally additional information, possibly including one or more purchase incentive offers for purchase of a product.

A purchase incentive offer is an offer for a benefit, such as a discount, upon purchase of a specified product.

In other examples of the first alternative, the payloadID corresponds to some value for some piece of information in the PM CS associated with the prescription order, or the payloadID corresponds to a combination of values for plural pieces of information in the PM CS associated with the prescription order. These pieces of information are generally defined in table 1, and are as follows: DrugID; DoctorID; NewRX; RefillRX; Refill#RX; PaymentType; Date processed; Time processed; NDC; Medication Name; Customer Name; Age; Date of Birth; Gender; Script Status; Payor; Payor Code; RX Number; Dispensed Qty; Refill Sequence; Language Indicator; Daily Supply; Days Supply; Original Fill Date; Expires Date; Refills Remaining; Unique Patient ID; Dr. Number; Monograph; State Code; Region; Retailer Division; Retailer Store; Patient Directions; Pharmacist Directions; NCPDP ID Number; BIN No.; Control No.; Agency; Group; Plan; Name Mask; Medicaid; Opt Out (HIPAA); and Duplicate. The corresponding payload provides printed information relating in some way to one or more of the values for the plural pieces of information in the PM CS associated with the prescription order, possibly including one or more purchase incentive offers for purchase of a product.

For instances where the payload is related to only one piece of information in the prescription order, the payloadID may be the value for that piece of information, or an encrypted version of that value. For example, the PayloadID may be any of the values or encrypted versions thereof for fields: DrugID; DoctorID; NewRX; RefillRX; Refill#RX; PaymentType; Date processed; Time processed; NDC; Medication Name; Customer Name; Age; Date of Birth; Gender; Script Status; Payor Code; RX Number; Dispensed Qty; Refill Sequence; Language Indicator; Daily Supply; Days Supply; Original Fill Date; Expires Date; Refills Remaining; Unique Patient ID; Number; Monograph; State Code; Region; Retailer Division; Retailer Store; Patient Directions; Pharmacist Directions; NCPDP ID Number; BIN No.; Control No.; Agency; Group; Plan; Name Mask: Medicaid; Opt Out (HIPAA); and Duplicate.

In a second alternative, a payloadID corresponds to a patient information (PatID). A PatID is associated with prescription order received in the pharmacy for the corresponding patient. In this alternative, the payloadID may be the PatID stored in the PM CS records, or an encrypted version of that PatID, EncPatID. In this alternative, the payload stored in the POS CS in association with the payloadID may have been predetermined based at least in part upon values for information in the PM CS associated with the prescription order from the same patient's prior prescription orders, or based upon such values for the patient's prior and current prescription orders. The values upon which the payload and payloadID are based are values for the same fields noted above as included in a record in the PM CS for a prescription order. The predetermination may be determined by any CS having access to at least part of the PM CS's patient records. The CS may be the PM CS or a central CS. That CS then transmits the payloadID to payload association to the POS CS where it is stored until the payloadID is read by the POS CS during a purchase transaction. The payload may include a purchase incentive offer, product (including drug product) advertising, and safety and use information about a drug associated with the prescription order.

In a variation on the second alternative where the PM CS performs the analysis and determination of payloadID to payload associations, the payloadID may correspond to a RecordID, Encrypted RecordID, PresID, or EncPresID.

In a preferred embodiment, the POS CS receives the co-payment to the current ongoing transaction involving the scanned prescription bar code and applies that co-payment to the transaction.

In a preferred embodiment, the POS CS does not save the PresID after the transaction is concluded.

In a preferred embodiment, the POS CS does save the recordID in association with other information for the transaction.

In a third embodiment, the POS CS requests from the PM CS an EncPatID associated with data it reads from papers attached to a filled prescription being purchased at a POS. Then, the POS CS uses the retrieved EncPatID as a PayloadID to determine if it has a Payload associated therewith. If so, it prints the payload if other conditions are met. In the third embodiment, the POS CS receives from the PM CS during the transaction, the EncPatID.

In a preferred embodiment, the POS CS captures, during purchase transactions, associations of EncPatID to NDC code, stores that information, and transmits that information to a central CS. The central CS analyzes the information and transmits back to the POS CS payloadIDs and associated payloads. Alternatively, the PM CS may perform these functions of the central CS.

In one aspect, the invention provides a system and computer implemented method for printing at a POS, comprising: determining in a PM CS of a pharmacy of a retail store a payloadID to association with a prescription order for a prescription ordered from said pharmacy; filling, in said pharmacy, said prescription, to provide a filled prescription; first printing, using a PM CS printer in said pharmacy, a first print that encodes first information associated with said filled prescription; attaching or physically associating with hardware or adhesive said first print with said filled prescription; during a purchase transaction in which said prescription is being purchased at a POS terminal of a POS CS of said retail store, reading said first print to determine said first information associated with said filled prescription; during said purchase transaction, using data lines for retrieving second information associated with said first information; and during said purchase transaction, second printing, using a printer at a POS of said POS CS, a second print including said second information in human understandable form.

BRIEF DESCRIPTION OF THE DRAWING

FIGS. 5A and 5B are a schematic design view of novel data structures of PM CS 60;

FIG. 6 is a schematic design view of novel data structures of POS CS 70;

FIG. 7 is a schematic design view of novel data structures of central CS 10 of FIG. 1;

DETAILED DESCRIPTION

Structures

Figure 1:
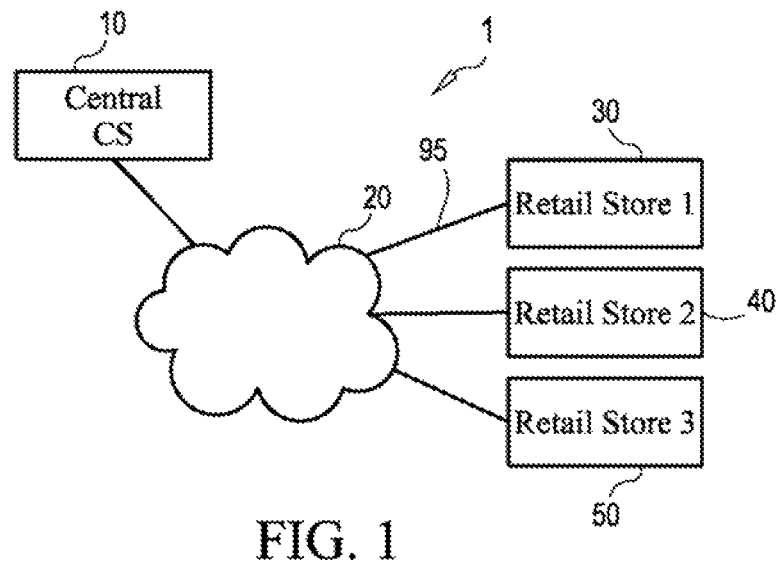
FIG. 1 is a schematic view of a computer network 1.

FIG. 1 shows a computer network including central CS 10, network 20, such as the Internet, and retail stores 30, 40, and 50. Lines connecting these elements represent data communication links, whether wired or wireless. Link 95 connects retail store 30 to network 20.

Figure 2:
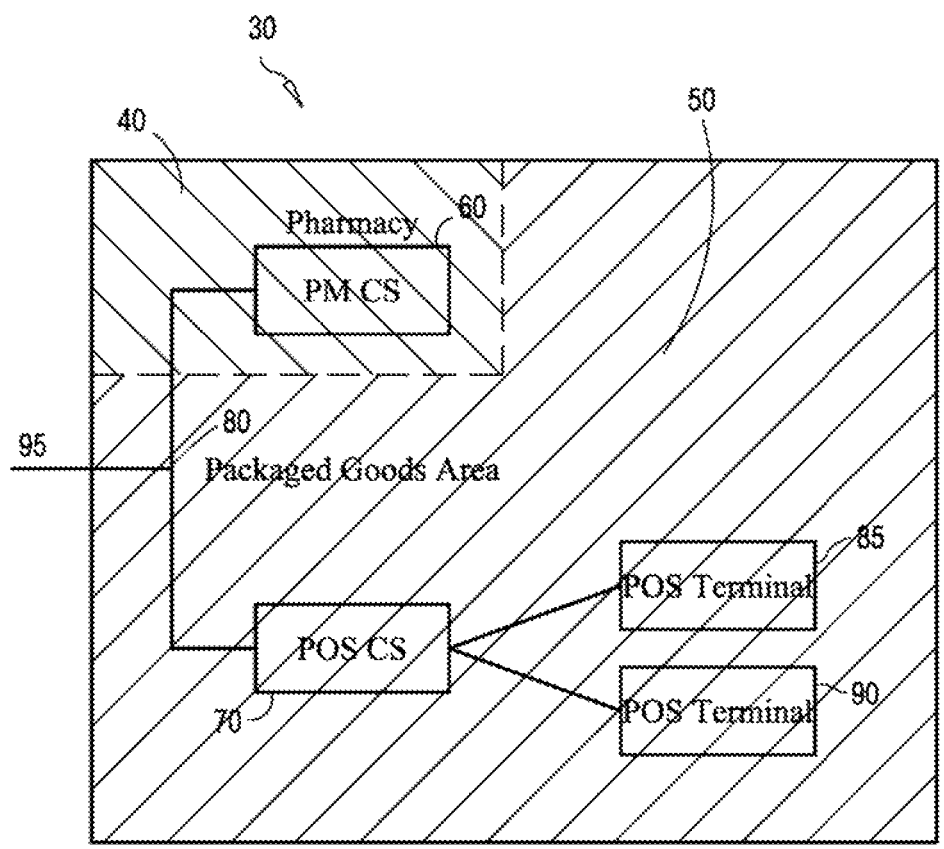
FIG. 2 is a schematic view of structure of retail store 30 of FIG. 1.

FIG. 2 shows retail store 30 including a region for use as a pharmacy wherein resides PM CS 60, a region for use as a packaged goods store including POS CS 70 having POS terminals 85 and 90, and a communication link 80 between PM CS 60 and POS CS 70. The pharmacy region may also have POS terminals connected to POS CS 70 therein. Communication link 80 preferably is a packet switched network connection.

Figure 3:
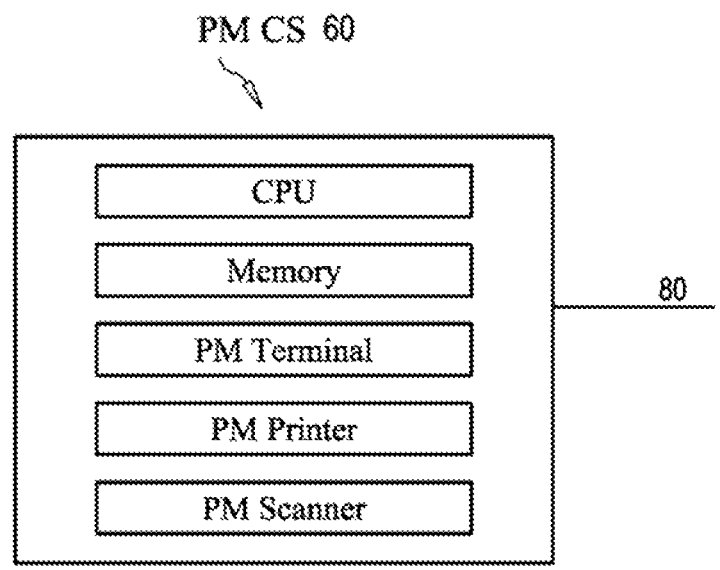
FIG. 3 is a schematic view of PM CS 60 of FIG. 2.

FIG. 3 shows elements of PM CS 60 including a CPU, memory, a PM terminal for data input and output, a PM printer for printing, and a PM scanner for scanning.

Figure 4:
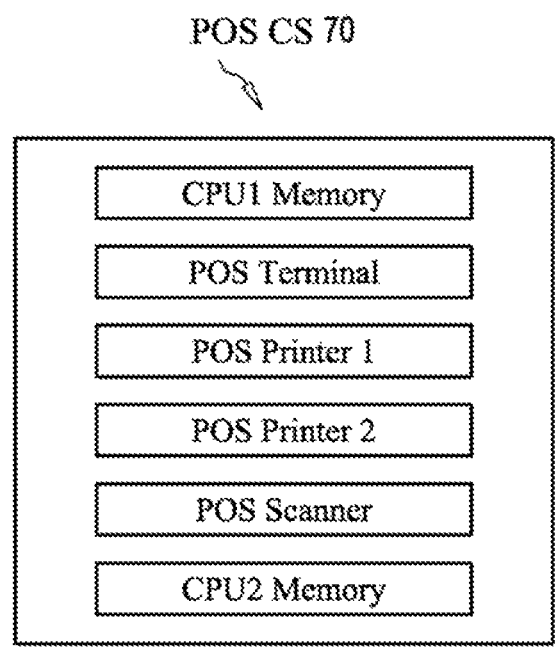
FIG. 4 is a schematic view of POS CS 70 of FIG. 2.

FIG. 4 shows elements of POS CS 70 including a first CPU, CPU 1, memory controlled by CPU1, a second CPU, CPU 2, and memory controlled by CPU2, a POS terminal, a first POS printer, POS printer 1, a second POS printer, POS printer 2, and a POS scanner. The POS terminal, printers, and scanner are located at the POS. The POS terminal typically includes a visual display and a keyboard for viewing and entering data. The POS scanner typically is linked to the POS terminal so that data scanned by the scanner is transmitted to the POS terminal. POS printer 1 typically prints register receipts for transactions as instructed by the POS terminal. POS printer 2 typically prints coupons and advertisements as instructed by the second CPU, CPU2. CPU1 and CPU2 may share memory or control their own memory, whether RAM or disk. In actual implementations CPU1 controls purchase and inventory functions, and CPU 2 controls marketing functions. CPU2 may obtain data entered into a POS terminal by listening in on the network line over which that data is transmitted to CPU1. CPU2 may control POS printer 2 to print marketing information, including the payloads discussed herein. Both POS printer 1, POS printer 2, scanner, and the POS terminal are at the same POS. There may be several POSs each having their own terminals and printers in each retail store.

Certain POS CS embodiments, have only a single printer at each POS capable of printing both register receipts and marketing materials and other information including the payloads discussed herein. Certain embodiments have a single CPU controlling both inventory and marketing. Certain embodiments have a CPU forming part of each POS terminal enabling the terminals to act independently of a CPU controlling store inventory.

FIGS. 5A and 5B show design views of novel data structures in the memory of PM CS 60 including a Pharmacy Patient Records Table 500, a De Identified Pharmacy Patient Records Table 510, Pharmacy Payload ID Table 520, a Pharmacy Prescription Label Printer Table 530, a Pharmacy Additional Information Printer Table 540, a Pharmacy Stock Table 550, an Encrypted Patent ID table 560, and an Encrypted Prescription ID table 570.

Pharmacy Patient Records Table 500 includes fields for PatID; PresID; Patient Information; NDC; Qnty; Order date; Filled Date; Purchase or Disposal Date; Copay amount; Department number; and recordID; and also for DoctorID; NewRX; RefillRX; Refill#RX; PaymentType; Date processed; Time processed; NDC; Medication Name; Customer Name; Age; Date of Birth; Gender; Script Status; Payor; Payor Code; RX Number; Dispensed Qty; Refill Sequence; Language Indicator; Daily Supply; Days Supply; Original Fill Date; Expires Date; Refills Remaining; Unique Patient ID; Dr. Number; Monograph; State Code; Region; Retailer Division; Retailer Store; Patient Directions; Pharmacist Directions; NCPDP ID Number; BIN No.; Control No.; Agency; Group; Plan; Name Mask; Medicaid; Opt Out (HIPAA); and Duplicate.

DE Identified Pharmacy Patient Records Table 510 includes fields for EncPatID; EncPresID; BF; NDC; Qnty; Order date; Filled Date; Purchase or Disposal Date; Copay amount; Department number; and recordID, and also the fields from DoctorID to Duplicate noted above for table 500. That is, table 510 is a version of the patient record from which it is not possible to identify the actual patient, unless one has access to the association of EncPatID to PatID, so that the patient record is "de-identified." Table 510 is a version of patient prescription records suitable for transmission to central CS 10, because it is de-identified.

Pharmacy Payload ID Table 520 includes fields for EncPresID; NDC; Qnty; Payload ID: Date1; Date2; and recordID. The Pharmacy payload table indicates what payloadID or payloadIDs to associate with a prescription order and with the prescription order's recordID. In addition to NDC, Pharmacy PayloadID Table 520 may include fields for all of the other data elements in De Identified Pharmacy Patient Records Table 510.

Pharmacy Prescription Label Printer Table 530 includes fields for PresID; Prescription Label Information (Patient name, medicine name, dosing information); Bar Code encoding at least one of Payload ID and recordID. Table 530 provides for encoding of the payloadID and/or recordID in a bar code.

Pharmacy Additional Information Printer Table 540 includes fields for NDC; and Additional Information relating to NDC medication. Table 540 allows PM CS 60 to print information relating to a drug in a prescription so that information can be attached to the prescription order.

Pharmacy Stock Table 550 includes fields for NDC; Unit Type; and Unit Quantity in stock. Table 550 enables PM CS 60 to track its drugs inventory.

Encrypted Patent ID table 560 includes fields for PatID; and EncPatID. Table 560 enables PM CS 60 to relate an encrypted PatID back to the corresponding PatID in table 500.

Encrypted Prescription ID table 570 includes fields for PresID; and EncPresID. Table 570 enables PM CS 60 to relate an EncPresID back to the corresponding unencrypted PresID in tables 500, 510, and 520.

FIG. 6 shows design views of novel data structures in the memory of POS CS 70 including Prescriptions Payload Table 600; RS Transaction Data Table 610; and RS POS Stock and Price Table 620.

RS Payload Table 600 includes fields for PayloadID; Payload; Date1; and Date2. This table allows POS CS 70 to determine payloads to print from payloadIDs. The date fields may be used to define a date range during which the payload should be printed for a corresponding payloadID.

RS Transaction Data Table 610 includes fields for TID; CID; Date; ProdID1; ProdID1 Price; ProdID1 Qnty; ProdID2; ProdID2 Price; ProdID2 Qnty; . . . ; Transaction Total Price; and Transaction Price Discounts. Here ". . . " indicates additional product descriptions for additional products associated with each transaction.

RS POS Stock and Price Table 620 includes fields for ProdID (UPC); Product Description; Stock Quantity; Price1; and Price2. This table allows the retail store to keep track of its stock. Price1 and price2 may reflect list price and discounted price for an item of a product.

FIG. 7 shows data structures in memory associated with central CS 10. These include many of the data structures similar to those associated with PM CS 60 and POS CS 70 wherein the only difference is an additional retail store identifier (RSID) added to data from each retail store in order to distinguish data from different retail stores from one another. These tables are: DE Identified Pharmacy Patient Records Table 510A; Pharmacy Payload ID Table 520A; Pharmacy Additional Information Printer Table 540A; RS Payload Table 600A; and the RS Transaction Data Table 610A.

FIG. 7 also shows additional data structures unique to central CS 10. Central CS 10 uses these tables to analyze and store prescription information and to determine payloads to associate with NDCs and encrypted prescription or PatIDs for a retail store. These include Payload Criteria Table 710; Payload Criteria Table 720; and Combined Payload table 730.

Payload Criteria Table 710 includes fields for RSID; NDC; and Payload. This table enables central CS 10 to determine what payloads to associated for NDCs for each retail store. Payload Criteria Table 710 may also criteria for all of the other fields in De Identified Pharmacy Patient Records Table 510A.

Payload Criteria Table 720 includes fields for NDC1; DATE1; NDC2; DATE2; NDC3; DATE3; . . . and Payload. This table provides criteria that central CS 10 uses to determine what payload to associate with one or more records of previously ordered prescriptions, a prescription history, associated with an identification, such as an encrypted PatID. CS 10 does so by determining if the prescription history meets the purchases of NDC1, NDC2, NDC3, etc, in the time periods DATE1, DATE2, DATE3, etc. Payload Criteria Table 720 may also criteria for all of the other fields appearing in the De Identified Pharmacy Patient Records Table 510A.

In one example showing use by central CS 10 of its tables, it compares prescription records in table 510A associated with a selected EncPatID to a record in Payload Table 720. Central CS 10 determines if the NDCs (or any other drug identification) and dates or date ranges of order or purchase, for records associated with an EncPatID, in table 510A, match values for the NDCs and dates or date ranges in a record from the Payload Criteria table 720. If they do, then CS 10 associates the payload identified in the record in Payload Criteria table 720 with the EncPatID and stores the association in a new record in Combined Payload table 730 along with the corresponding RSID. Central CS 10 may also generate and store in the same record in Combined Payload table 730 a payloadID and dates for the fields date1 and date2. If central CS determines that the payload should only be provided upon purchase of a certain prescription order appearing in table 510A, it may also store the corresponding EncPresID in the same record in Combined Payload Table 730. The fields date1 and date2 may be used by the POS CS as start and end dates for period only during which the payload will be printed.

In another example showing use by central CS 10 of its tables, it compares prescription records in table 510A associated with a selected EncPatID to a record in Payload Table 720 as in the foregoing example, but also determines if the age field is greater than 30 and gender field is female. If so, it also provides an incentive for a medicine approved for treating bone mass loss.

In another example showing use by central CS 10 of its tables, it compares prescription records in table 510A associated with a selected EncPatID to a record in Payload Table 720 as in the foregoing example, but also determines if the "payor" field is "cash". If so, it also provides an incentive for a generic version of the medicine (which is typically less expensive) than the prescription's specified medicine.

In another example showing use by central CS 10 of its tables, it compares prescription records in table 510A associated with a selected EncPatID to a record in Payload Table 720 as in the foregoing example, but also determines if the "Dr. Number" is one of a specified set of values. If so, it also provides advertising or an incentive for visit to a specified doctor or medical organization. Typically, the specified doctor or medical organization will be one having expertise in the same field of medicine that employs the drug contained in the prescription order.

In another example showing use by central CS 10 of its tables, it compares prescription records in table 510A associated with a selected EncPatID to a record in Payload Table 720 as in the foregoing example, but also determines if the NDC is "00071-0156-23" which is the NDC for the trademarked drug Lipitor, which is known to reduce cholesterol. If so, the payload includes a coupon for a brand of aspirin, and printed information about the ability of aspirin to reduce heart disease.

Methods

Figure 8:
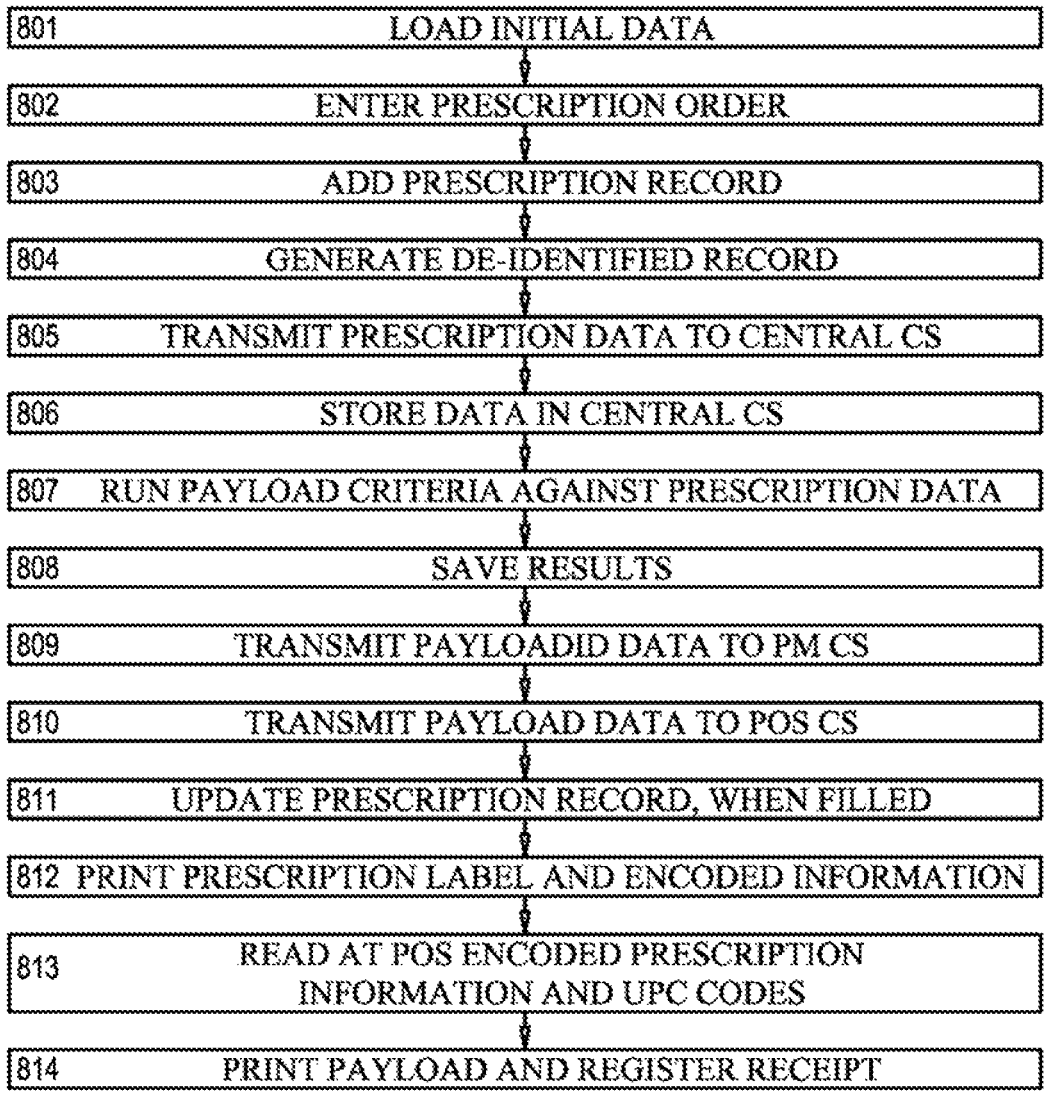
FIG. 8 is a flow chart showing initial steps of various method embodiments.

FIG. 8 shows steps of methods of use.

Initially, tables storing data used by the method are populated. This includes populating the Pharmacy Patient Records Table 500, and the Payload Criteria Tables 710, 720. Other data tables are also populated, including the pharmacy and retail store stock tables 550 and 620. See step 801.

A patient brings a prescription to the pharmacy, ordering the prescription. The PM CS 60's terminal reads the prescription data. The data may be entered manually using a keyboard, mouse, or any other input device. The data includes patient name, drug, and quantity or dosage information. See step 802.

PM CS 60 generates a record in Pharmacy Patient Records Table 500. It identifies the PatID from the patient information, the NDC from the drug information, assigns a PresID, and enters the order date. PM CS 60 generates a RecordID and stores that in the record. See step 803.

Either PM CS 60 or a third party determines a copay amount, and PM CS 60 enters that amount in the record for the prescription.

PM CS 60 generates a corresponding record in De Identified Pharmacy Patient Records Table 510 from the record added to table 500. It does so by encrypting the PatID and the PresID resulting in EncPatID and EncPresID values. It also removes the Patient Information as shown symbolically in table 510 by the blank field BF instead of a Patient Information field. See step 804.

PM CS 60 transmits table 510 to central CS 10. See step 805.

Central CS 10 stores in table 510A the data records from table 510 and also a RSID associated with PM CS 60 and POS CS 70. See Step 806.

Central CS 10 employs its criteria data in tables 710 and 720 to determine what payloads to provide to the purchaser of the prescription. See step 807.

Central CS 10 saves in Combined Payload table 710 the results of its application of criteria to prescription data and also save subsets of the data stored in table 710 in its Pharmacy PayloadID table 520A and its RS Payload table 600A. See step 808.

Central CS 10 transmits newly added records associated with the RSID for PM CS 60 in Pharmacy PayloadID table 520A to PM CS 60. PM CS 60 adds those records to its table 520. See step 809.

Central CS 10 transmits newly added records in associated with the RSID for POS CS 70 in RS Payload Table 600A to POS CS 70. POS CS 70 adds those records to its RS Payload Table 600. See step 810.

A pharmacist or the like prepares the prescription, and enters into the PM CS 60 that the prescription was filled. In response, PM CS 60 enters the current date or date and time in the "Filled date" field in the Pharmacy Patient Records Table 500. See step 811.

In response, PM CS 60 also prints information for attachment to the filled prescription. This information includes prescription label information such as patient name, medication, dosing. This information also includes encoding of either or both of the RecordID for the prescription and a payloadID. See step 812. In many pharmacy systems, step 812 occurs after step 803 and before step 804.

In order to generate the print including a payloadID, before printing, PM CS 60 query's Pharmacy PayloadID table 520 with any of the PresID or the EncPresID or the NDC, or data in any of the other fields identified above in table 510, for the prescription order, and retrieves from the query for printing one or more corresponding payloadIDs. Alternatively, table 520 (and 520A) may be designed to store the PatID or EncPatID, in which case PM CS 60 may query based upon PatID or EncPatID for a corresponding payloadID.

In order to print the RecordID, PM CS 60 retrieves the corresponding RecordID from table 500, 510 or 520.

Someone, such as a pharmacist of a purchaser, tenders the filled prescription and associated printed information at a POS terminal 85, for purchase.

POS CS 70 reads the encoded information on the printed information at POS terminal 85. POS CS 70 reads, for example using a bar code scanner located at or part of POS terminal 85 if the encoded information is encoded in a printed bar code. It may alternatively use a magnetic media reader. The information encoded in print form on the papers associated with the prescription may also include a copay amount, a drugID, such as an NDC, and a department code (such as a code indicating the pharmacy department). See step 813.

If the information read by the POS CS 70 from the paper associated with the filled prescription includes the copay amount, then POS CS 70 includes that amount in calculating the cost of the purchase transaction. POS CS 70 also reads at terminal 85 product identifications for any other products being purchased in the same purchase transaction.

Finally, POS CS 70 prints at the POS the payload or payloads identified for the transaction, and prints a register receipt for the transaction. See step 814.

Figure 9:
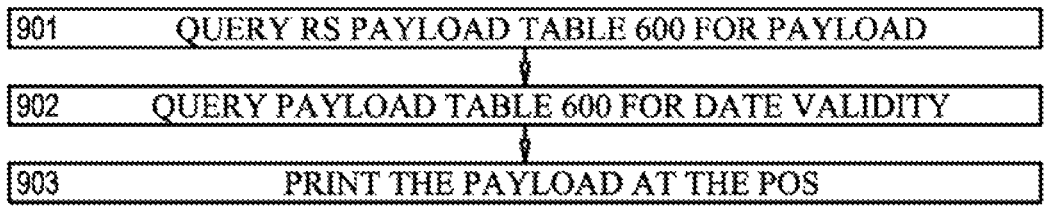
FIG. 9 is a flow chart showing steps of the first embodiment subsequent to those described in FIG. 8.

FIG. 9 relates to the first set of embodiments. In the first set of embodiments, the encoded prescription information includes a payloadID. The encoded information may also include EncPatID. Upon POS CS 70 reading the payloadID, it queries RS Payload table 600 to determine the corresponding payload. See step 901.

POS CS 70 may also query table 600 to determine if the current date is between the values in the Date1 and Date2 fields stored in association with that payloadID and Payload, and only if so, print the payload. See step 902.

POS CS 70 then prints that payload at the POS. See step 903.

Figure 10:
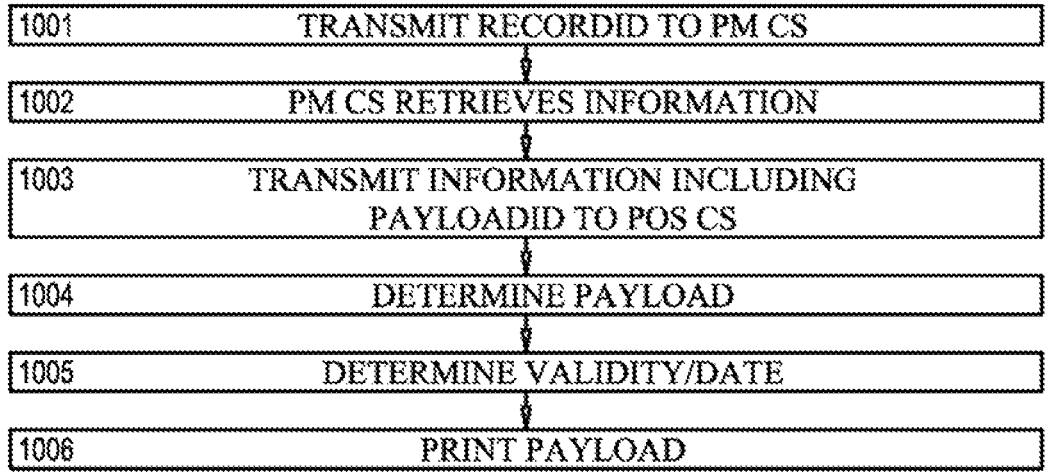
FIG. 10 is a flow chart showing steps of the second embodiment subsequent to those described in FIG. 8.

FIG. 10 relates to the second set of embodiments. In the second set of embodiments, the printed encoded information associated with the filled prescription includes a Record ID. The recordID has a value that is unique among recordID values to only one prescription record. Upon POS CS 70 reading at POS terminal 85 a RecordID from the papers attached to or associated with the filled prescription, POS 70 transmits via data link 80 that RecordID to PM CS 60. See step 1001. The PresID and the EncPresID may serve as a RecordID.

In response, PM CS 60 queries its Pharmacy Payload Table 520 and table 500 or 510 to determine payloadID, NDC (or an equivalent drugID), copay amount and either PresID or EncPresID. PM CS 60 may also retrieve any of the other information from the corresponding record in De Identified Pharmacy Patient Records table 510. See step 1002.

PM CS 60 transmits the retrieved information via data link 80 to POS CS 70. See step 1003.

PM CS 60 may also transmit to POS CS 60 the EncPatID. POS CS 70 then determines the payload associated in its RS Payload table 600 with that payloadID. See step 1004.

Again, POS CS 70 may only print the payload if it also determines that the current date is between the dates stored in the date1 and date2 fields for that payloadID in table 600. See step 1005.

POS CS 70 then prints the payload. See step 1006.

In either of the first and second set of embodiments, the EncPatID, NDC, and copay amount, and any other information for the corresponding prescription order stored in De Identified Pharmacy Patient Records table 510, may be encoded in the printed material printed by the PM CS 60 and read at the POS at the time of purchase. Any of the other information contained in the De Identified Pharmacy Patient Records Table 510 may be transmitted from the PM CS 60 to the POS CS 70, either as print or via electronic data transfer.

In either embodiment, the POS CS 70 preferably logs some or all of the purchase transaction data.

Figure 11:
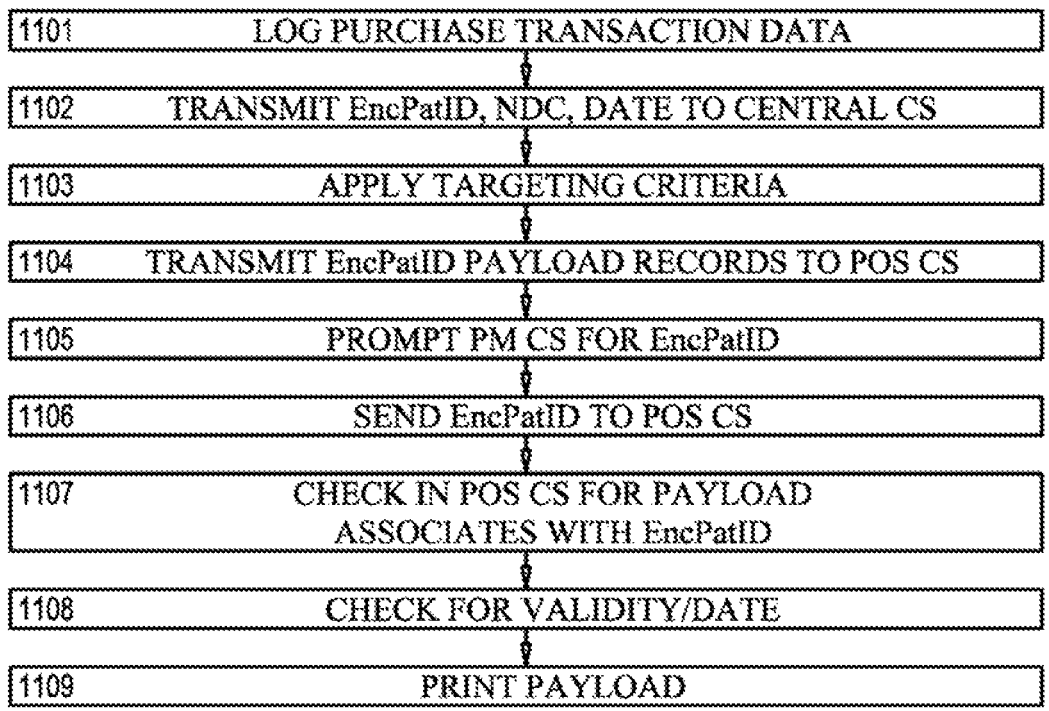
FIG. 11 is a flow chart showing steps of the third embodiment subsequent to those described in FIG. 8.

FIG. 11 relates to logging and use of the purchase transaction data, and to the third embodiment.

POS CS 70 logs purchase transaction data. See step 1101.

This data includes UPCs for the non prescription items being purchased, their purchase prices, the pharmacy department code, copay amount for the filled prescription, NDC (or drugID) code for the filled prescription, the transaction total amount, identification of the purchaser, if presented, such as frequent shopper card number, a portion of frequent shopper card number, an encrypted version of a frequency shopper card number, a portion of credit card number used by the purchaser during the transaction, and other information defining the transaction. It may also include the PresID or EncPresID. The logged data may also include any of the other information contained in the DE Identified Pharmacy Patient Records Table 510.

In one alternative, POS CS 70 transmits to central CS 10 logged data including in association with one another for a purchase transaction, NDC or drugID, date, and EncPatID, the transmitted data may also include any of the other information contained in the De Identified Pharmacy Patient Records Table 510. See step 1102.

Central CS 10 may analyze this data and previously received data for the EncPatID from the same retail store by applying its criteria to it to determine new payloadIDs and corresponding Payloads to associated with the EncPatID. See step 1103.

Central CS 10 may subsequently transmit records pairs of an EncPatID and a PayloadID, or EncPatID and a Payload, to POS CS 70. See step 1104.

Each time a customer purchases a pharmacy prescription at a POS of the store, POS CS 70 prompts the PM CS 60 for the associated EncPatID. See step 1105. The PM CS 60 returns the EncPatID to the POS CS 70. See step 1106.

POS CS 70 then checks to determine if that EncPatID is stored in association with a PayloadID in its data base. See step 1107.

If so, it preferably determines if the current date is within a specified date range. See step 1108.

If so, it then prints the payload. Se step 1109.

The retail store computer system performs all of these operations, while the person who presented the filled prescription for purchase is at the POS involved in the purchase transaction including the new prescription.

As disclosed, several fields in the database tables are redundant to provide for a single disclosure of sequence of operational steps and alternative embodiments of the methods. The actual data structures are therefore exemplary all elements therein are clearly not required for any particular mode of operation. Moreover, the description herein of all steps for all method embodiments does not mean all of those steps are necessary or essential for any one embodiment. A reader should instead look to the appended claims to determine the scope of protection.

The following table 1 presents elements of information in the PM CS associated with a prescription record.

TABLE 1

DoctorID - Identification of a doctor associated with a prescription;
NewRX - The prescription order is for a new prescription.
RefillRX - The prescription order is for a refill of a prescription.
Refill#RX - The number of the refill (first, second, third, etc.) of the prescription order.
PaymentType - Type of payment (credit card, check, cash. etc.)
Date processed - Date PatientLink printed. A PatientLink is a trademark associating with Catalina Health Resources and/or Catalina Marketing Corporation the goods and services of "[p]romoting the sale of health-related goods and services of others through the distribution of coupons, premiums, rebates, discounts, samples, incentives, promotions, advertisements and messages." PatientLink herein refers to the printed material associated with a prescription label containing that type of health-related information.
Time processed - Time PatientLink printed.
NDC - An 11 digit National Drug Code
Medication Name - This information is printed on a PatientLink. May contain actual drug name.
Customer Name - Patient name, which is required to personalize a PatientLink.
Age - Patient age.
Date of Birth - Used to calculate patient age.
Gender - M—Male, F—Female, U—unknown.
Script Status - N—New Script, R—Refill
Payor - Third party payer name. CASH if customer paid.
Payor Code - Third party payer code. CASH if customer paid.
RX Number - Prescription number, which is printed on a PatientLink.
Dispensed Qty. - Quantity of medication dispensed, i.e. pill count.
Refill Sequence - Field contains 0 for new scripts. On the first refill this field would contain 1.
Language Indicator - English or Spanish language (or other language) preference.
Daily Supply - Daily quantity of consumption of medication. i.e. 3 pills.
Days Supply - Number of days this script is intended to last.
Original Fill Date - This is the date that the prescription originally got filled.
Expires Date - This is the date that the original prescription expires.
Refills Remaining - Total refills less the ones that have already been filled.
Unique Patient ID - Pharmacy system's patient identifier.
Dr. Number - Dr.'s identification number.
Monograph - Monograph for PatientLink.
State Code - State code for store location.
Region - Retailer's region.
Retailer Division - Division ID to aid in triggering division specific programs.
Retailer Store - Store ID to aid in triggering store specific programs.
Patient Directions - Patient directions to be printed on a PatientLink.
Pharmacist Directions - Pharmacist directions to be printed on a PatientLink.
NCPDP ID Number - National council for prescription Drug Programs ID.
BIN No. - Third party.
Control No. - Third party plan.
Agency - The legal relationship between an agent and a principal.
Group - Insurance that provides coverage for several people under one contract, called a master contract.
Plan - A plan document identifies the benefits the participants are to receive and the requirements they must meet to become entitled to those benefits.
Name Mask - A flag to tell our software to mask patient name with "Valued Customer" or the like.
Medicaid - A flag to indicate if a patient is paying with Medicaid.
Opt Out (HIPAA) - A flag to tell our software this patient does not want to receive PatientLink.
Duplicate - A flag to indicate if this is a duplicate transaction, i.e. label only, call doctor, etc.

We claim:

1. A method for printing, at a retail computer of a retail store that includes a pharmacy section having a pharmacy and a retail section distinct from the pharmacy section, information relating to a pharmacy prescription ordered at a pharmacy computer of the pharmacy, the retail computer being coupled to a point of sale printer that prints receipts for retail transactions being paid for at the retail computer and the pharmacy computer being coupled to a pharmacy printer that prints pharmacy information for prescriptions being filled at the pharmacy, the method comprising:

receiving, at a pharmacy computer for processing prescription orders for filling prescriptions at the pharmacy of the retail store, a prescription order;

determining, at the pharmacy computer, information to be provided based on the prescription order;

generating, at the pharmacy computer using the pharmacy printer, a first print that encodes data comprising an identifier associated with the information to be provided;

reading, at a retail computer for checking out retail transactions to be paid for at the retail computer, the data from the first print;

determining, at the retail computer, the identifier based on the data read from the first print;

querying, at the retail computer, a database stored at a memory of the retail computer using the identifier, wherein the database pre-stores a plurality of information to be provided in in association with corresponding identifiers, the plurality of information to be provided including the information to be provided and the corresponding identifiers including the identifier;

obtaining, at the retail computer, (i) the information to be provided based on the querying, and (ii) an identification of at least one retail item to be purchased at the retail computer based on a retail transaction occurring at the retail computer in association with the prescription order; and generating, at the retail computer using a point of sale printer at a point of sale for printing receipt information related to payment for the retail transaction at the retail computer, a second print that comprises the information to be provided and a receipt for purchase of the at least one retail item.

2. The method of claim 1, wherein:
the identifier comprises an identifier that identifies the information to be provided.

3. The method of claim 2, wherein the information to be provided comprises information describing safety and use of a drug.

4. The method of claim 2, wherein the information to be provided comprises an incentive to purchase a product.

5. The method of claim 1, wherein the data further comprises a prescription identifier that identifies the prescription order, a copay amount, and a drug identifier, the method further comprising:

reading, at the retail computer from the first print, the prescription identifier, the copay amount, and the drug identifier.

6. The method of claim 1, wherein the identifier comprises a record identifier that identifies a record associated with the prescription order stored at the pharmacy computer, the method further comprising, transmitting, at the retail computer, the record identifier to the pharmacy computer;

determining, at the pharmacy computer, an identifier that identifies the information to be provided based on the record identifier;

transmitting, at the pharmacy computer, the identifier that identifies the information to be provided to the retail computer; and obtaining, at the retail computer, the information to be provided based on the identifier that identifies the information to be provided.

7. The method of claim 6, wherein the information to be provided comprises information describing safety and use of a drug.

8. The method of claim 6, wherein the information to be provided comprises an incentive for purchasing a product.

9. The method of claim 6, further comprising:

retrieving, at the pharmacy computer, a prescription identifier, a copay amount, and a drug identifier associated with the prescription order; and transmitting, at the pharmacy computer, the prescription identifier, the copay amount, and the drug identifier to the retail computer.

10. The method of claim 1, further comprising:

transmitting, at the retail computer to a central computer that is coupled to the pharmacy computer and the retail computer, a purchase transaction record comprising an encrypted patient identifier and a drug identifier associated with the prescription order; and associating, at the central computer, the encrypted patient identifier with at least one payload based on criteria applicable to the drug identifier.

11. The method of claim 1 further comprising:

transmitting, at the pharmacy computer, a plurality of de-identified prescription records to a central computer that is coupled to the retail computer and the pharmacy computer;

determining, at the central computer, a plurality of information to be provided based on the de-identified prescription records;

assigning, at the central computer, an identifier for individual ones of the plurality of information to be provided; and transmitting, at the central computer to the retail computer, the plurality of information to be provided and corresponding identifiers.

12. A system for printing, at a retail computer of a retail store that includes a pharmacy section having a pharmacy and a retail section distinct from the pharmacy section, information relating to a pharmacy prescription ordered at a pharmacy computer the pharmacy, the retail computer being coupled to a point of sale printer that prints receipts for retail transactions being paid for at the retail computer and the pharmacy computer being coupled to a pharmacy printer that prints pharmacy information for prescriptions being filled at the pharmacy, the system comprising:

a pharmacy computer for processing prescription orders for filling prescriptions at the pharmacy of the retail store, the pharmacy computer configured to:
receive a prescription order;
determine information to be provided based on the prescription order;
generate, via the pharmacy printer, a first print that encodes data comprising an identifier associated with the information to be provided; and a retail computer for checking out retail transactions to be paid for at the retail computer, the retail computer coupled to a point of sale printer and configured to:
read the data encoded in the first print;

determine the identifier based on the data read from the first print;
query a database stored at a memory of the retail computer using the identifier, wherein the database stores a plurality of information to be provided in association with corresponding identifiers, the plurality of information to be provided including the information to be provided and the corresponding identifiers including the identifier;
obtain the (i) information to be provided based on the query, and (ii) an identification of at least one retail item to be purchased at the retail computer based on a retail transaction occurring at the retail computer in association with the prescription order; and
generate, via the point of sale printer at a point of sale for printing receipt information related to payment for the retail transaction at the retail computer, a second print that comprises the information to be provided and a receipt for purchase of the at least one retail item.

13. The system of claim 12, wherein the identifier comprises an identifier that identifies the information to be provided.

14. The system of claim 13, wherein the information to be provided comprises information describing safety and use of a drug.

15. The system of claim 13, wherein the information to be provided comprises an incentive for purchasing a product.

16. The system of claim 12, wherein the retail computer is further configured to:
print via the point of sale printer a register receipt comprising transaction data of a purchase transaction checked out by the retail computer.

17. The system of claim 12, wherein the information to be provided comprises a prescription identifier that identifies the prescription order, a copay amount, and a drug identifier, and wherein the retail computer is further configured to:
read, at the retail computer during a purchase transaction checked out by the retail computer, from the first print, the prescription identifier, the copay amount, and the drug identifier.

18. The system of claim 12, wherein the identifier comprises a record identifier that identifies a record associated with the prescription order stored at the pharmacy computer, and
wherein the retail computer is further configured to:
transmit the record identifier to the pharmacy computer; and
wherein the pharmacy computer is configured to:
determine an identifier that identifies the information to be provided based on the record identifier; and
transmit the identifier that identifies the information to be provided to the retail computer, wherein the retail computer obtains the information to be provided based on the identifier that identifies the information to be provided.

19. The system of claim 18, wherein the payload comprises information describing safety and use of a drug.

20. The system of claim 18, wherein the information to be provided comprises an incentive for purchasing a product.

21. The system of claim 18, wherein the pharmacy computer is further configured to:
retrieve a prescription identifier, a copay amount, and a drug identifier; and
transmit the prescription identifier, the copay amount, and the drug identifier to the retail computer.

22. The system of claim 18, further comprising:
a central computer configured to:
receive, from the retail computer, a purchase transaction record comprising an encrypted patient identifier and a drug identifier associated with the prescription order; and
associate the encrypted patient identifier with the information to be provided based on criteria applicable to the drug identifier.

23. The system of claim 12, wherein:
the pharmacy computer is further configured to:
transmit a plurality of de-identified patient prescription records to a central computer; and wherein:
the central computer is configured to:
determine a plurality of information to be provided based on the plurality of de-identified patient prescription records;
assign an identifier to each of the plurality of payloads; and
transmit the plurality of information to be provided and their corresponding identifiers to the retail computer.

24. A method of providing information at a retail computer of a retail store that includes a pharmacy section having a pharmacy and a retail section distinct from the pharmacy section, the pharmacy having a pharmacy computer that processes a prescription order and a pharmacy printer that prints a first printed medium used to obtain information to be provided by a point of sale printer based on a prescription order received at the pharmacy and the retail computer being coupled to a point of sale printer that prints receipts for retail transactions being checked out by the retailer computer, the method comprising:
storing, in a memory of a retail computer, a plurality of records in association with corresponding identifiers, wherein the plurality of records include the information to be provided, and the corresponding identifiers include the identifier;
reading, by the retail computer used to check out retail transactions to be paid for at the retail computer, a first printed medium that was printed at a pharmacy by the pharmacy printer in association with a prescription order filled at the pharmacy;
determining, by the retail computer, an identifier encoded by the first printed medium and associated with the information to be provided based on the prescription order;
querying, at the retail computer, the database stored at the memory of the retail computer using the identifier;
obtaining, by the retail computer, (i) the information to be provided based on the querying, and (ii) an identification of at least one retail item to be purchased at the retail computer based on a retail transaction occurring at the retail computer in association with the prescription order; and
generating, by the retail computer at the point of sale printer at a point of sale for printing receipt information related to payment for the retail transaction at the retail computer, a second printed medium that comprises the information to be provided and a receipt for purchase of the at least one retail item.

25. The method of claim 24, wherein the plurality of information to be provided and the plurality of identifiers are received from a pharmacy computer of a pharmacy at the retail store.

26. The method of claim 24, wherein the plurality of information to be provided and the plurality of identifiers are received from a central computer.

27. The method of claim 24, wherein the identifier comprises a record identifier that identifies a pharmacy record associated with the prescription order, the method further comprising:

communicating, by the retail computer, the record identifier to a pharmacy computer of a pharmacy at the retail store;

receiving, by the retail computer from the pharmacy computer, an identifier that identifies the information to be provided; and obtaining, by the retail computer, the information to be provided based on the identifier that identifies the information to be provided.

28. A method of providing a printed medium used to obtain information to be provided that is associated with a prescription order processed at a pharmacy of a retail store, reads the printed medium, and provides the information to provided based on the printed medium, the retail store including a pharmacy section having a pharmacy and a retail section distinct from the pharmacy section, the method comprising:

receiving, by a pharmacy computer for processing prescription orders for filling prescriptions at the pharmacy of the retail store, a prescription order;

determining, by the pharmacy computer, information to be provided based on the prescription order;

storing, by the pharmacy computer, (i) an association between the information to be provided and an identifier that identifies the information to be provided, and (ii) a second association between the identifier and a second identifier; and generating, by the pharmacy computer at a pharmacy printer, a printed medium comprising encoded data used to obtain the information to be provided at a retail computer that reads the printed medium, wherein the encoded data comprises the second identifier;

receiving, by the pharmacy computer, the second identifier back from the retail computer, wherein the retail computer obtained the second identifier from the printed medium;

identifying, by the pharmacy computer, the identifier based on the second association; and providing, by the pharmacy computer, the identifier that identifies the information to be provided to the retail computer, wherein the retail computer obtains the information to be provided based on the identifier.

29. The method of claim 28, wherein the encoded data comprises identifier that identifies the information to be provided.

30. The method of claim 28, wherein the encoded data comprises a record identifier associated with the prescription order and stored at the pharmacy computer.

31. The method of claim 30, further comprising:

receiving, at the pharmacy computer from the retail computer, the record identifier;

determining, at the pharmacy computer, the identifier that identifies the information to be provided based on an association between the identifier that identifies the information to be provided and the record identifier; and transmitting, at the pharmacy computer to the retail computer, the identifier that identifies the information to be provided, wherein the retail computer uses the identifier that identifies the information to be provided to obtain the information to be provided.

32. The method of claim 28, further comprising:

associating, by the pharmacy computer, a plurality of information to be provided individually associated with at least one of a plurality of identifiers; and transmitting, by the pharmacy computer, the plurality of information to be provided and the plurality of identifiers to a retail computer for storage at the retail computer.

33. A system of providing prescription-related information to different retail locations, each retail location comprising a pharmacy computer used to facilitate prescription orders and a retail computer used to process retail transactions, the system comprising:

a memory programmed to store: (1) first prescription-related information and second prescription-related information, and (2) at least one criterion used to determine whether the first prescription-related information and/or the second prescription-related information should be provided to a given retail location;

a computer comprising one or more processors programmed with computer program instructions to:

receive first prescription history information from a first retail location that includes a first pharmacy computer and a first retail computer, wherein the first prescription history information includes a first prescription drug identifier and a first retail identifier that identifies the first retail location;

receive second prescription history information from a second retail location that includes a second pharmacy computer and a second retail computer, wherein the second prescription history information includes a second prescription drug identifier and a second retail identifier that identifies the first retail location;

determine that the first retail location should receive the first prescription-related information based on the at least one criterion and the first prescription drug identifier;

determine that the second retail location should receive the second prescription-related information based on the at least one criterion and the second prescription drug identifier;

provide the first prescription-related information to both the first pharmacy computer and to the first retail computer based on the first retailer identifier step, the first pharmacy computer and the first retail computer each include their own copy, wherein the first prescription-related information is queryable at either or both the first pharmacy computer and the first retail computer; and provide the second prescription-related information to both the second pharmacy computer and to the second retail computer based on the second retailer identifier such that the second pharmacy computer and the second retail computer each can query include their own copy such that the second prescription-related information is queryable at the second pharmacy computer and the second retail computer.

34. The system of claim 33, wherein the first prescription history information comprises a date of purchase indicating when the first prescription drug was purchased and the at least one criterion further comprises a time period, and wherein the determination that the first retail location should receive the first prescription-related information is based further on the date falling within the time period.

35. The system of claim 33, wherein the first prescription history information comprises a date of purchase indicating when the first prescription drug was purchased and the at least one criterion further comprises a time period, and wherein the determination to associate the prescription-related information with the first prescription history information is based further on the date falling within the time period.

36. The system of claim 33, wherein the memory is further programmed to store a plurality of incentives and at least one incentive criterion used to determine whether to provide an incentive, and wherein the computer is further programmed to:
   identify at least a first incentive to provide based on the at least one incentive criterion; and
   include the first incentive with the first prescription-related information such that the incentive is provided along with the first prescription-related information.

37. The system of claim 33, wherein the at least one criterion comprises a match between the first prescription drug identifier and a drug identifier associated with the first incentive.

38. The system of claim 33, wherein the at least one criterion comprises a patient demographic criterion such that the first incentive is based on a demographic of the patient.

39. The system of claim 33, wherein the at least one criterion comprises a generic drug criterion such that the first incentive is based on a brand of a drug.

40. The system of claim 33, wherein the at least one criterion comprises a doctor recommendation criterion such that the first incentive is based on a drug.

41. The system of claim 33, wherein the at least one criterion comprises a medical organization recommendation criterion such that the first incentive is based on a drug.

42. The system of claim 33, wherein the at least one criterion comprises an information on a drug criterion such that the first incentive is based on a drug.

\* \* \* \* \*